US00PP30439P2

(12) United States Plant Patent
Koppe

(10) Patent No.: US PP30,439 P2
(45) Date of Patent: Apr. 23, 2019

(54) ***BEGONIA* PLANT NAMED 'KRHAIPE01'**

(50) Latin Name: ***Begonia* x *hiemalis***
Varietal Denomination: KRHAIPE01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 15/732,403

(22) Filed: Nov. 6, 2017

(51) Int. Cl.
*A01H 5/02* (2018.01)

(52) U.S. Cl.
USPC ..... Plt./348

(58) Field of Classification Search
USPC ..... Plt./263.1, 344, 348
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Begonia* plant named 'KRHAIPE01' characterized by its upright to outwardly spreading and mounded plant habit; moderately vigorous growth habit; freely flowering habit; double type flowers that are light salmon red in color and held above and beyond the foliar plane; and excellent postproduction longevity.

2 Drawing Sheets

Botanical designation: *Begonia* x *hiemalis*.
Cultivar denomination: 'KRHAIPE01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRHAIPE01'.

The new *Begonia* plant is a product of a planned breeding program conducted by the Inventor in Ermelo, The Netherlands. The objective of the breeding program is to create new vigorous *Begonia* plants with excellent postproduction longevity and attractive flower color.

The new *Begonia* plant originated from a cross-pollination made by the Inventor in Ermelo, The Netherlands in January, 2013 of a proprietary selection of *Begonia* x *tuberhybrida* hybrid identified as code number KV11K1915-004, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in January, 2014. Asexual reproduction of the new *Begonia* plant by terminal vegetative cuttings taken in a controlled greenhouse environment in Ermelo, The Netherlands since April, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRHAIPE01'. These characteristics in combination distinguish 'KRHAIPE01' as a new and distinct *Begonia* plant:

1. Upright to outwardly spreading and mounded plant habit.
2. Moderately vigorous growth habit.
3. Freely flowering habit.
4. Double type flowers that are light salmon red in color and held above and beyond the foliar plane.
5. Excellent postproduction longevity.

Plants of the new *Begonia* differ primarily from plants of the female parent selection in flower color as plants of the female parent selection have yellow orange-colored flowers.

Plants of the new *Begonia* differ primarily from plants of the male parent selection in flower color as plants of the male parent selection have light red purple-colored flowers. In addition, plants of the *Begonia* have double type flowers whereas plants of the male parent selection have single type flowers.

Plants of the new *Begonia* can be compared to plants of *Begonia* x *hiemalis* 'Dark Britt', not patented. In side-by-side comparisons conducted in Ermelo, The Netherlands, plants of the new *Begonia* differ primarily from plants of 'Dark Britt' in flower color as plants of 'Dark Britt' have orange-colored flowers. In addition, plants of the new *Begonia* have larger and more fully double flowers than plants of 'Dark Britt'.

Plants of the new *Begonia* can also be compared to plants of *Begonia* x *hiemalis* 'Reina', disclosed in U.S. Plant Pat. No. 19,336. In side-by-side comparisons conducted in Ermelo, The Netherlands, plants of the new *Begonia* differ primarily from plants of 'Reina' in flower size as plants of 'Reina' have smaller. In addition, plants of the new *Begonia* and 'Reina' differ in flower color as plants of 'Reina' have dark orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRHAIPE01' grown in a container.

The photograph on the second sheet are close up views of the upper (right) and lower (left) surfaces of typical leaves and flowers of 'KRHAIPE01', and in the center of the photograph is a close-up view of typical flower buds.

DETAILED BOTANICAL DESCRIPTION

The aforementioned photographs and following observations and measurements describe plants grown during the late spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRHAIPE01'.

Parentage:

*Female, or seed, parent*.—Proprietary selection of *Begonia* x *tuberhybrida* hybrid identified as code number KV11K1915-004, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to outwardly spreading and mounded plant habit; overall plant shape, broadly obovate to nearly globular.

*Growth habit*.—Moderately vigorous growth habit and moderate growth rate; suitable for 12-cm and larger containers; under optimal environmental and cultural conditions, usually about nine weeks are required to produce proportional plants in 12-cm containers.

*Branching habit*.—Moderately freely branching with about four primary branches developing per plant.

*Plant height, soil level to top of foliar plane*.—About 23.6 cm.

*Plant height, soil level to top of floral plane*.—About 28.3 cm.

*Plant width*.—About 38 cm.

*Lateral branches*.—Length: About 10.9 cm. Diameter: About 0.9 cm to 1 cm. Internode length: About 3.4 cm. Strength: Moderately strong. Aspect: About 30° from vertical. Texture and luster: Initially, sparsely pubescent and becoming smooth and glabrous with development; glossy. Color, developing: Close to 144A. Color, developed: Close to 146A; proximally, closer to 148A.

*Leaves*.—Arrangement: Alternate, simple. Length: About 13.4 cm. Width: About 11.3 cm. Shape: Ovate, asymmetrical. Apex: Acute. Base: Hastate. Margin: Crenate to dentate; slightly undulate. Texture and luster, upper surface: Smooth, glabrous; moderately velvety; matte. Texture and luster, lower surface: Sparsely pubescent along venation; slightly velvety; slightly glossy. Venation pattern: Laciniate. Color: Developing leaves, upper surface: Slighter darker than 143A. Developing leaves, lower surface: Close to 138B. Fully expanded leaves, upper surface: Darker than between 139A and 147A; venation, close to 143B. Fully expanded leaves, lower surface: Close to 191B; towards the margins, tinged with close to 181C; venation, close to 146C. Petioles: Length: About 7 cm. Diameter: About 5 mm to 5.5 mm. Strength: Low, flexible. Texture and luster, upper and lower surfaces: Sparsely pubescent; moderately glossy. Color, upper surface: Close to 152A. Color, lower surface: Close to 152A; distally on developed leaves, strongly tinged with close to 180A. Stipules: Length: About 8mm. Width: About 1.2 cm. Shape: Roughly lunate. Apex: Obtuse. Base: Broadly cuneate. Margin: Finely ciliate. Texture and luster, upper and lower surfaces: Smooth, glabrous; moderately glossy. Color, upper and lower surfaces: Close to 145A.

Flower description:

*Flower appearance and flowering habit*.—Double type rotate flowers with four tepals and numerous tepaloids; flowers arranged in axillary compound cymes; freely flowering habit with typically about eleven flowers per cyme and about 400 flowers and flower buds developing per plant; many cymes in flower simultaneously; flowers positioned above and beyond the foliar plane and face upright to outwardly.

*Natural flowering season*.—Plants begin flowering about five weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about five to six weeks in an interior environment.

*Fragrance*.—None detected.

*Inflorescence height*.—About 14 cm.

*Inflorescence diameter*.—About 6.4 cm.

*Flowers*.—Shape: Rotate, fully double type. Diameter: About 6.1 cm. Depth (height): About 2.4 cm.

*Flower buds*.—Length: About 1.9 cm. Diameter: About 0.5 cm to 2.2 cm. Shape: Reniform, flattened. Texture and luster: Glabrous; slightly velvety; matte. Color: Close to 37B; fading towards the base to close to 37D.

*Tepals*.—Quantity and arrangement per flower: Usually about four per flower arranged in two whorls. Length, lower tepals: About 3.4 cm. Width, lower tepals: About 4.2 cm. Length, upper tepals: About 2.9 cm. Width, upper tepals: About 3.2 cm. Shape, all tepals: Reniform. Apex, all tepals: Rounded. Base, all tepals: Truncate. Margin, all tepals: Entire; moderately undulate. Texture and luster, upper surface, lower tepals: Smooth, glabrous; moderately velvety; matte. Texture and luster, lower surface, lower tepals: Smooth, glabrous; moderately velvety; slightly glossy. Texture and luster, upper and lower surfaces, upper tepals: Smooth, glabrous; moderately velvety; matte. Color, lower tepals: When opening, upper surface: Close to 39B; fading towards the base to close to 24C to 24D. When opening, lower surface: Close to 39B; fading towards the base to close to 36A. Fully opened, upper surface: Close to 38A; fading towards the base to close to 8B; venation, similar to lamina color; colors do not change with development. Fully opened, lower surface: Close to 38B; fading towards the base to close to 8B; venation, similar to lamina color; colors do not change with development. Color, upper tepals: When opening, upper surface: Close to 32C; fading towards the base to close to 24B. When opening, lower surface: Close to 37B; fading towards the base to close to 37C. Fully opened, upper surface: Close to 37A; fading towards the base to close to 13A; proximal margins, close to 28B; venation, similar to lamina color; colors do not change with development. Fully opened, lower surface: Close to 37C; venation, similar to lamina color; colors do not change with development.

*Tepaloids*.—Quantity and arrangement per flower: Typically about eleven per flower clustered at the center of the flower. Length: About 0.9 cm to 2.1 cm. Width: About 0.4 cm to 1.7 cm. Shape: Obovate. Apex: Obtuse. Base: Cuneate. Margin: Entire; slightly undulate. Texture and luster, upper surface: Smooth, glabrous; moderately velvety; matte. Texture and luster, upper surface: Smooth, glabrous; slightly velvety; matte. Color: When opening, upper surface: Close to 32C; fading towards the base to close to 10A. When opening, lower surface: Close to 37B. Fully opened, upper surface: Close to 38A; fading towards the base to close to 8B; venation, similar to lamina color; color does not change with development. Fully opened, lower surface: Close to 38B; fading towards the base to close to 8B; venation, similar to lamina color; color does not change with development.

*Peduncles*.—Length: About 6.4 cm. Diameter: About 5 mm to 6 mm. Strength: Moderately strong. Aspect: About 40° from lateral branch axis. Texture and luster: Sparsely pubescent; moderately glossy. Color: Close to 144A to 144B.

*Pedicels*.—Length: About 1.8 cm. Diameter: About 2.5 mm. Strength: Moderately strong. Aspect: About 35° from peduncle axis. Texture and luster: Moderately pubescent; glossy. Color: Close to 161A.

*Flower bracts*.—Quantity per flower: Two. Length: About 1.4 cm. Width: About 1.8 cm. Shape: Roughly reniform. Apex: Obtuse to bluntly acute. Base: Broadly cuneate. Margin: Finely ciliate. Texture and luster, upper and lower surfaces: Smooth, glabrous; slightly glossy. Color, upper and lower surfaces: Close to 146D; venation, similar to lamina color.

*Reproductive organs*.—Stamens and pistils: None observed; male and female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRHAIPE01' as illustrated and described.

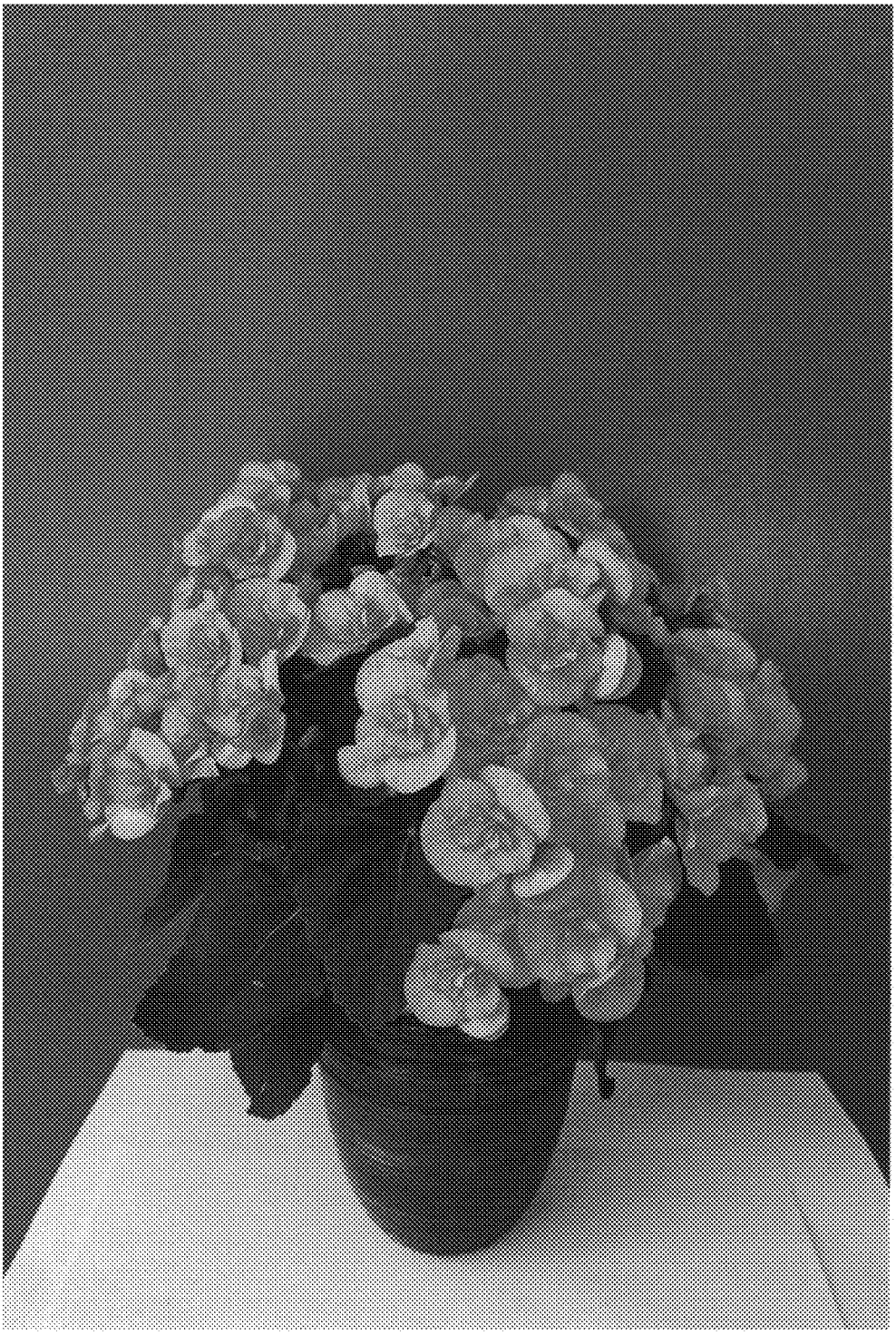

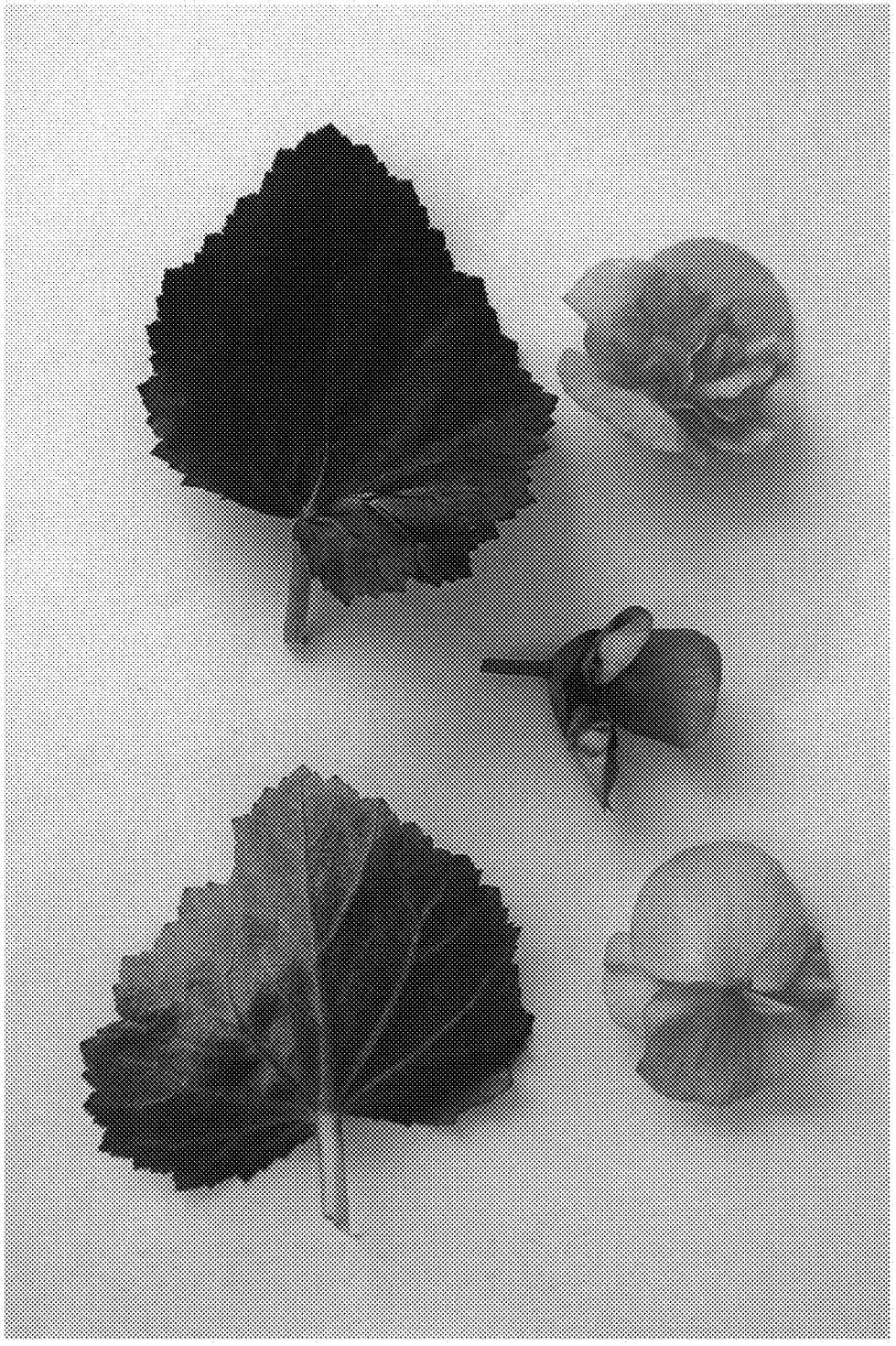

* * * * *